US011234594B2

(12) United States Patent
Amir et al.

(10) Patent No.: US 11,234,594 B2
(45) Date of Patent: Feb. 1, 2022

(54) SYSTEMS AND METHODS FOR ADAPTIVE SKIN TREATMENT

(71) Applicant: E.S.I Novel Ltd., Herzeliya Pituach (IL)

(72) Inventors: Haim Amir, Ramat-HaSharon (IL); Arie Wainberg, Yokneam Ilit (IL); Anat Kaphan, Zikhron-Yaakov (IL)

(73) Assignee: E.S.I Novel Ltd., Herzeliya Pituach (IL)

( * ) Notice: Subject to any disclaimer, the term of this patent is extended or adjusted under 35 U.S.C. 154(b) by 713 days.

(21) Appl. No.: 15/539,165

(22) PCT Filed: May 19, 2016

(86) PCT No.: PCT/IL2016/050528
§ 371 (c)(1),
(2) Date: Jun. 23, 2017

(87) PCT Pub. No.: WO2016/203461
PCT Pub. Date: Dec. 22, 2016

(65) Prior Publication Data
US 2018/0014777 A1    Jan. 18, 2018

Related U.S. Application Data

(60) Provisional application No. 62/175,461, filed on Jun. 15, 2015, provisional application No. 62/175,463, (Continued)

(51) Int. Cl.
*G16H 80/00*    (2018.01)
*A61B 5/00*    (2006.01)
(Continued)

(52) U.S. Cl.
CPC .......... *A61B 5/0002* (2013.01); *A61B 5/0077* (2013.01); *A61B 5/442* (2013.01);
(Continued)

(58) Field of Classification Search
CPC ... A61B 5/4839; A61B 5/0002; A61B 5/0077; A61B 5/442; A61B 5/443; A61B 5/444;
(Continued)

(56) References Cited

U.S. PATENT DOCUMENTS

2003/0065294 A1*  4/2003  Pickup ............... A61M 37/0084
                                                                              604/304
2003/0084914 A1    5/2003  Simon
(Continued)

FOREIGN PATENT DOCUMENTS

CN          1642594        7/2005
CN          1738664        2/2006
(Continued)

OTHER PUBLICATIONS

International Search Report and the Written Opinion dated Sep. 11, 2016 From the International Searching Authority Re. Application No. PCT/IL2016/050528.
(Continued)

*Primary Examiner* — Amanda K Hulbert
*Assistant Examiner* — Natasha Patel

(57) ABSTRACT

According to an aspect of some embodiments of the present invention there is provided a method of dynamically adapting a facial treatment based on a current facial skin profile, comprising: using at least one sensor for measuring at least one current value of at least one variable skin characteristic of facial skin of a patient; acquiring at least one personal skin characteristic of facial skin of the patient; calculating a current facial skin status of the patient according to the at least one personal skin characteristic and the at least one current value; determining instructions to operate a treatment applicator according to the current facial skin status; and instructing the treatment applicator according to the instructions.

21 Claims, 5 Drawing Sheets

Related U.S. Application Data filed on Jun. 15, 2015, provisional application No. 62/175,464, filed on Jun. 15, 2015, provisional application No. 62/175,466, filed on Jun. 15, 2015.

(51) Int. Cl.

| | |
|---|---|
| *G16H 40/20* | (2018.01) |
| *G16H 50/20* | (2018.01) |
| *G16H 20/30* | (2018.01) |
| *G16H 20/40* | (2018.01) |
| *G16H 70/20* | (2018.01) |
| *A61M 35/00* | (2006.01) |
| *A61N 1/40* | (2006.01) |
| *A61N 5/06* | (2006.01) |
| *G06N 20/00* | (2019.01) |
| *A61N 5/067* | (2006.01) |
| *G16H 10/60* | (2018.01) |
| *A61B 17/00* | (2006.01) |
| *A61B 18/00* | (2006.01) |

(52) U.S. Cl.
CPC .............. *A61B 5/443* (2013.01); *A61B 5/444* (2013.01); *A61B 5/445* (2013.01); *A61B 5/4836* (2013.01); *A61B 5/4839* (2013.01); *A61B 5/68* (2013.01); *A61B 5/6898* (2013.01); *A61B 5/7267* (2013.01); *A61B 5/7425* (2013.01); *A61M 35/003* (2013.01); *A61N 1/40* (2013.01); *A61N 5/0616* (2013.01); *G16H 20/30* (2018.01); *G16H 20/40* (2018.01); *G16H 40/20* (2018.01); *G16H 50/20* (2018.01); *G16H 70/20* (2018.01); *G16H 80/00* (2018.01); *A61B 5/7475* (2013.01); *A61B 2017/00057* (2013.01); *A61B 2017/00132* (2013.01); *A61B 2017/00141* (2013.01); *A61B 2017/00221* (2013.01); *A61B 2018/0075* (2013.01); *A61B 2018/00732* (2013.01); *A61B 2576/02* (2013.01); *A61N 5/067* (2021.08); *A61N 2005/0626* (2013.01); *G06N 20/00* (2019.01); *G16H 10/60* (2018.01)

(58) Field of Classification Search
CPC ......... A61B 5/445; A61B 5/4836; A61B 5/68; A61B 5/6898; A61B 5/7267; A61B 5/7425; G16H 20/30; G16H 40/20; G16H 50/20; G16H 80/00; A61M 35/003; A61N 1/40; A61N 5/0616; G06F 16/325; G06F 30/27; G06N 20/20; G16C 20/70; G06K 9/62; G16B 40/00

See application file for complete search history.

(56) References Cited

U.S. PATENT DOCUMENTS

| | | | |
|---|---|---|---|
| 2006/0248946 A1 | 11/2006 | Howell et al. | |
| 2007/0021357 A1* | 1/2007 | Tobia | A61K 31/192 514/23 |
| 2007/0231255 A1* | 10/2007 | Barolet | A61N 5/062 424/1.11 |
| 2008/0270175 A1 | 10/2008 | Rodriguez et al. | |
| 2010/0185064 A1* | 7/2010 | Bandic | G16H 50/20 600/306 |
| 2010/0210993 A1* | 8/2010 | Flyash | A61N 1/36034 604/20 |
| 2011/0218464 A1* | 9/2011 | Iger | A61B 18/14 601/2 |
| 2011/0295400 A1* | 12/2011 | Samain | G06Q 10/06 700/97 |
| 2013/0103017 A1* | 4/2013 | Weckwerth | A61B 18/203 606/9 |
| 2013/0302078 A1 | 11/2013 | Edgar | |
| 2014/0005736 A1* | 1/2014 | Geheb | A61B 5/4836 607/7 |
| 2014/0074193 A1* | 3/2014 | Luzon | A61B 18/203 607/89 |
| 2014/0313303 A1 | 10/2014 | Davis et al. | |
| 2015/0025420 A1* | 1/2015 | Slayton | A61N 7/00 601/2 |
| 2015/0057622 A1 | 2/2015 | Hyde et al. | |
| 2015/0177059 A1* | 6/2015 | Lian | G01T 1/02 702/19 |
| 2015/0257828 A1* | 9/2015 | Tankovich | A61B 18/203 604/20 |

FOREIGN PATENT DOCUMENTS

| | | |
|---|---|---|
| CN | 203369905 | 1/2014 |
| CN | 103917272 | 7/2014 |
| CN | 104586364 | 5/2015 |
| EP | 2786673 | 10/2014 |
| JP | 2013-019909 | 9/2013 |
| KR | 10-1277450 | 6/2013 |
| WO | WO 03/076000 | 9/2003 |
| WO | WO 2004/062728 | 7/2004 |
| WO | WO 2007/022095 | 2/2007 |
| WO | WO 2013/040443 | 3/2013 |
| WO | WO 2013/184127 | 12/2013 |
| WO | WO 2016/203461 | 12/2016 |

OTHER PUBLICATIONS

Supplementary European Search Report and the European Search Opinion Dated Aug. 2, 2018 From the European Patent Office Re. Application No. 16811130.0. (8 Pages).
Notification of Office Action and Search Report Dated Oct. 8, 2019 From the State Intellectual Property Office of the People's Republic of China Re. Application No. 201680018355.0 and Its Translation of Office Action Into English. (15 Pages).
International Preliminary Report on Patentability Dated Dec. 28, 2017 From the International Bureau of WIPO Re. Application No. PCT/IL2016/050528. (8 Pages).
Translation Dated Nov. 11, 2019 of Request for Examination Dated Oct. 25, 2019 From the Federal Service for Intellectual Property, Federal Government Budgetary Institution, Federal Institute of Industrial Property, FIPS of the Russian Federation Re. Application No. 2017128027. (16 Pages).
Request for Examination and Search Report Dated Oct. 25, 2019 From the Russian Agency for Industrial Property, Patents, and Trade Marks, Federal Institute of industrial Property, FIPS of the Russian Federation Re. Application No. 2017128027. (18 Pages).
Notice of Reasons for Rejection Dated Mar. 31, 2020 From the Japan Patent Office Re. Application No. 2017-543393 and Its Translation Into English. (7 Pages).
Communication Pursuant to Article 94(3) EPC Dated Sep. 17, 2020 From the European Patent Office Re. Application No. 16811130.0. (5 Pages).
Examination Report Under Sections 12 & 13 of the Patents Act, 1970 and the Patents Rules, 2003 Dated Sep. 23, 2020 From the Government of India, Intellectual Property India, Patents, Designs, Trade Marks, Geographical Indications, The Patent Office Re. Application No. 201727025334. (6 Pages).
Notice of Reasons for Rejection Dated Oct. 20, 2020 From the Japan Patent Office Re. Application No. 2017-543393. (1 Page).

\* cited by examiner

SYSTEMS AND METHODS FOR ADAPTIVE SKIN TREATMENT

RELATED APPLICATIONS

This application is a National Phase of PCT Patent Application No. PCT/IL2016/050528 having International filing date of May 19, 2016, which claims the benefit of priority under 35 USC § 119(e) of U.S. Provisional Patent Applications Nos. 62/175,461, 62/175,463, 62/175,464, and 62/175,466 all filed on Jun. 15, 2015. The contents of the above applications are all incorporated by reference as if fully set forth herein in their entirety.

BACKGROUND

The present invention, in some embodiments thereof, relates to providing skin treatments and, more specifically, but not exclusively, to systems and methods to determine instructions to operate a skin treatment applicator to provide customized treatment to a body part of a patient.

Different treatments are available to treat the patient's skin, for example, to clean, moisturize, nurture, heat, and cool the skin.

SUMMARY

According to an aspect of some embodiments of the present invention there is provided a method of dynamically adapting a facial treatment based on a current facial skin profile, comprising: using at least one sensor for measuring at least one current value of at least one variable skin characteristic of facial skin of a patient; acquiring at least one personal skin characteristic of facial skin of the patient; calculating a current facial skin status of the patient according to the at least one personal skin characteristic and the at least one current value; determining instructions to operate a treatment applicator according to the current facial skin status; and instructing the treatment applicator according to the instructions.

Optionally, calculating the current facial skin status of the patient is performed based on code executing a machine learning algorithm trained using a training set storing at least one facial skin characteristic for each of a plurality of different patients. Optionally, the training set stores at least one calculated current facial skin status of each of the plurality of different patients, calculated based on at least one measured current value for at least one variable skin characteristic and at least one personal skin characteristic of each respective patient.

Optionally, the method further comprises acquiring at least one environmental condition characteristic; wherein the current facial skin status of the patient is calculated according to the at least one personal skin characteristic and the at least one current value and the at least one environmental condition characteristic, the at least one environment condition characteristic selected from the group consisting of: humidity forecast, temperature forecast, overcast forecast, pollution level, radiation level, and ultraviolet index forecast. Optionally, the method further comprises acquiring location data indicative of a current location of the patient and using the current location for acquiring the at least one environmental condition characteristic.

Optionally, the method further comprises performing an analysis of historical records indicative of locations of the patient in a predefined period which precedes the calculating of the current facial skin status; wherein the current facial skin status of the patient is calculated according to the at least one personal skin characteristic and the at least one current value and an outcome of the analysis.

Optionally, the method further comprises performing an analysis of scheduling records indicative of future locations of the patient in a predefined period which proceeds the calculating of the current facial skin status; wherein the current facial skin status of the patient is calculated according to the at least one personal skin characteristic and the at least one current value and an outcome of the analysis.

Optionally, the instructing comprises instructions to input at least one selected substance or at least one removable capsule comprising at least one selected substance.

Optionally, the at least one sensor comprises an image sensor.

Alternatively or additionally, the at least one sensor comprises a skin moisture detector.

Alternatively or additionally, the at least one sensor comprises a skin elasticity detector.

Optionally, the at least one personal skin characteristic is selected from the group consisting of: skin color, skin shade, genetic information, and skin type.

Optionally, the instructions to operate the treatment applicator include instructions to control at least one of: amount, type, concentration, and combination of at least one applied substance.

Optionally, the instructions to operate the treatment applicator include instructions to adapt an applied light or laser transmission pattern. Optionally, at least one parameter of the applied light or laser transmission pattern is adapted, the at least one parameter selected from the group consisting of: frequency, timing, phase, and amplitude.

Optionally, the instructions to operating the treatment applicator include instructions to adapt a radiofrequency (RF) transmission pattern, by adapting at least one parameter selected from the group consisting of: frequency, timing, phase, and amplitude.

Optionally, the instructions to operating the treatment applicator include instructions to adapt an ultrasonic transmission pattern, by adapting at least one parameter selected from the group consisting of: frequency, timing, phase, amplitude, cleaning intensity, and pore widening intensity.

According to an aspect of some embodiments of the present invention there is provided a system for dynamically adapting a facial treatment based on a current facial skin profile, comprising: at least one sensor for measuring at least one current value of at least one skin characteristic of the facial skin of the patient; a treatment applicator comprising at least one applicator element for applying a treatment to facial skin of a patient; a communication unit for receiving data from a database storing data associated with a plurality of patients; a program store storing code; and a processor coupled to the at least one sensor, to the communication unit, and to the program store for implementing the stored code, the code comprising: code instructions for acquiring at least one personal skin characteristic of facial skin of the patient from the at least one current value, code instructions for calculating a current facial skin status of the patient according to the at least one personal skin characteristic and to the data associated with the plurality of patients, code instructions for determining treatment instructions to operate a treatment applicator according to the current facial skin status; and code instructions for instructing the treatment applicator according to the treatment instructions.

Optionally, the treatment applicator includes the at least one sensor, wherein the treatment applicator further comprises an applicator communication interface for wirelessly communicating with a mobile device that includes the program store and stored code, wherein the treatment applicator transmits the at least one current value to the mobile device and receives the determined treatment instructions from the mobile device.

Optionally, the treatment applicator further comprises a substance container for storing at least one removable capsule each comprising at least one cosmetic substance for application by at least one applicator element according to the determined treatment instructions. Optionally, the treatment applicator further comprises: a tag reader that reads a tag located on the at least one removable capsule storing information of the cosmetic substance stored in the respective capsule; and code instructions stored in a memory for execution by at least one processor, the code instructions identify each at least one removable capsule as new or continued capsule. Optionally, the treatment applicator further comprises code instructions stored in a memory for execution by at least one processor, the code instructions calculate the remaining amount of the at least one cosmetic substance in the respective at least one removable capsule or a number of remaining treatments according to the calculated remaining amount of the at least one cosmetic substance. Optionally, the determined treatment instructions include instructions to control for each cosmetic substance, at least one of: an amount, a concentration, a type of administration, and a combination with at least one another cosmetic substance. Optionally, the training set stores at least one calculated current facial skin status of each of the plurality of different patients, is calculated based on at least one measured current value for at least one variable skin characteristic and at least one personal skin characteristic of each respective patient.

Optionally, calculating the current facial skin status of the patient is performed based on code executing a machine learning algorithm trained using a training set storing at least one facial skin characteristic for each of a plurality of different patients.

Optionally, the system further comprises code to acquire at least one environmental condition characteristic by accessing a server over a network; wherein the current facial skin status of the patient is calculated according to the at least one personal skin characteristic and the at least one current value and the at least one environmental condition characteristic, the at least one environment condition characteristic selected from the group consisting of: humidity forecast, temperature forecast, overcast forecast, pollution level, radiation level, and ultraviolet index forecast. Optionally, the system further comprises a geographical location element that provides location data indicative of a current location of the patient, and further comprising code that uses the current location for acquiring the at least one environmental condition characteristic. Optionally, the system further comprises code that performs an analysis of historical or scheduled records indicative of locations of the patient in a predefined period which precedes or proceeds, respectively, the calculating of the current facial skin status or the treatment instructions; wherein the current facial skin status or the treatment instructions of the patient are calculated according to the at least one personal skin characteristic and the at least one current value and an outcome of the analysis.

Optionally, the system further comprises code to present a message on a display to a user to input at least one selected cosmetic substance or at least one removable capsule comprising at least one selected cosmetic substance.

Optionally, the at least one sensor comprises an image sensor.

Optionally, the at least one sensor comprises a skin moisture detector and a skin elasticity detector.

Optionally, the at least one personal skin characteristic is selected from the group consisting of: skin color, skin shade, genetic information, and skin type.

Optionally, the instructions to operate the treatment applicator include instructions to adapt an applied light or laser transmission pattern by the at least one applicator element, based on at least one parameter selected from the group consisting of: frequency, timing, phase, and amplitude.

Optionally, the instructions to operate the treatment applicator include instructions to adapt at least one parameter of a radiofrequency (RF) transmission pattern or an ultrasonic transmission pattern by the at least one applicator element, the at least one parameter selected from the group consisting of: frequency, timing, phase, and amplitude.

According to an aspect of some embodiments of the present invention there is provided a capsule for use with a system for providing a facial treatment, the capsule comprising: a cosmetic substance and an electronically-readable identification, the system for providing the facial treatment comprising: at least one sensor for measuring at least one current value of at least one skin characteristic of the facial skin of the patient; and a treatment applicator comprising at least one applicator element for applying substance from the capsule to the facial skin of a patient.

According to an aspect of some embodiments of the present invention there is provided a method of dynamically adapting a facial treatment based on an estimated exposure to skin damage factors, comprising: performing an analysis of at least one of: historical records indicative of locations of a patient in a predefined historical period, a routine of the patient; scheduling records indicative of future locations of the patient in a predefined future period; calculating a treatment plan for the patient according to an outcome of the analysis; determining instructions to operate a treatment applicator according to the treatment plan; and instructing the treatment applicator according to the instructions; wherein at least one of the historical records and the scheduling records are gathered using a monitoring module executed by at least one processor of a mobile device associated with the patient.

Optionally, calculating the treatment plan is performed based on code executing a machine learning algorithm trained using a training set of at least one of historical records and scheduling records associated with the same patient for which the instructions are determined.

Optionally, calculating the treatment plan is performed based on code executing a machine learning algorithm trained using a training set of at least one of historical records and scheduling records associated with a plurality of other patients different than the patient for which the instructions are determined.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DETAILED DESCRIPTION

Figure 1:
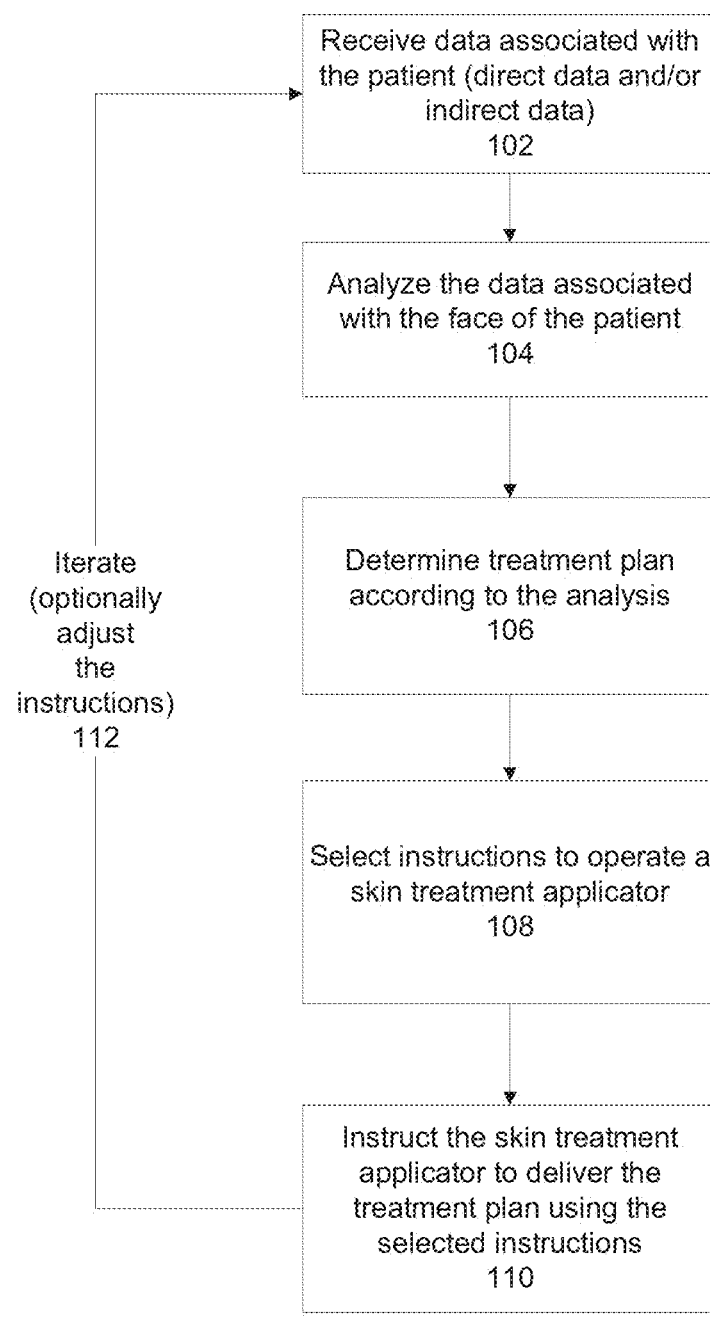
FIG. 1 is a method for dynamically adapting instructions provided to a skin treatment applicator providing a facial treatment to a face of a patient, in accordance with some embodiments of the present invention.

The present invention, in some embodiments thereof, relates to providing skin treatments and, more specifically, but not exclusively, to systems and methods to determine instructions to operate a skin treatment applicator to provide customized treatment to a face of a patient.

An aspect of some embodiments of the present invention relates to systems and/or methods (e.g., code executed by a processing unit) that dynamically adapt instructions for operating a skin treatment applicator providing a facial treatment to a face of a patient. The instructions for operating the skin treatment applicator to provide the facial treatment are customized to the patient receiving the treatment. The facial treatment (which is used to determine the instructions) may be customized for the patient. Optionally, the instructions are selected and/or dynamically adapted according to the current location of the skin treatment applicator in front of a facial segment of the face of the patient. Different treatments may be selected for different facial segments. Alternatively or additionally, the instructions are selected and/or dynamically adapted according to a current skin profile of the patient. The instructions may be customized to the patient receiving the treatment and/or to the current skin status of the patient, for example, different treatments may be determined for the same patient at different times. Alternatively or additionally, the instructions are selected and/or dynamically adapted according to estimated exposure to skin damage factors of the face of the patients. The instructions may be selected according to high or low accumulated or predicted damage due to the skin damage factors.

Optionally, the treatment and/or the instructions are determined based on data collected from multiple patients (using "big data" information collections and methods for processing the same). The data from the multiple patients is used to train a machine learning method (e.g., classifier) to determine the treatment plan and/or instructions based on input parameters as described herein, for example the current skin profile and estimated exposure to skin damage. The classifier may be trained using skin parameters and sensor measurements, treatment outputs (which may be manually entered by the respective patients or care givers and/or automatically measured by sensors) to determine the treatment most likely to succeed for the current patient, based on experiences of other patients, to whom the patient is determined to be similar, for example in the effect of the treatment or in other similarity measurements.

The systems and/or methods described herein provide a technical solution to the technical problem of determining instructions for operating a skin treatment applicator to apply a facial treatment to the skin of a patient, which are customized at least according to the skin of the patient. Many different skin treatment modalities are available, for example, application of one or more cosmetic substances (creams, lotions), and application of energy (e.g., light, laser, ultrasound, radiofrequency, heating, and cooling). The same (or similar) treatment may not work (or not work well) for different patients, for example, due to different skin types, different skin pigmentations, exposure to different environmental conditions, and/or different ages of the patients. The same (or similar) treatment may not work (or not work well) for the same patient under different external conditions, for example, when applied after the patient was exposed to sun during a vacation, and/or when the local environmental conditions change significantly. The same (or similar) treatment may not work (or not work well) for the same patient under different facial conditions, for example, after a sunburn, the presence of acne, and/or new skin pigmentation (e.g., after sun tanning). The same (or similar) treatment may not work (or not work well) for the same patient at different times of the day and/or days of the week, for example, office workers may need to apply higher amounts and/or values of sun protection factor (SPF) on weekends (in which they are outside exposed to the sun while performing recreational activities) than on weekdays (in which they are in the office away from the sun). The same (or similar) treatment may not work well for the same patient as the patient ages. The same (or similar) treatment may not work (or not work well) for different parts of the face of the same patient, for example, the forehead, nose, and chin may be oiler than the cheeks and therefore require different treatments than the cheeks. Treatments may interact with each other in positive ways (e.g., achieve a synergistic effect) or in negative ways (e.g., reduce the effective treatment when used together, or chemically react in dangerous ways). Each treatment may be applied in different ways, for example, in different amounts, and at different frequencies. As such, the number of possible facial skin treatments based on the possible combinations of the different treatment conditions and modalities is extremely large, making selection of the particular treatment for each patient difficult. The systems and/or methods described herein gather and analyze customized data associated with the patient, to select a customized treatment plan. The treatment plan may be selected based on experiences with other patients and/or with the same patient, based on automated machine learning processes.

The systems and/or methods described herein tie mathematical operations (e.g., calculating the location of the skin treatment applicator, analyzing sensor outputs to determine a current value of a variable skin characteristic, and using machine learning methods to analyze records of locations of the patient) to the ability of a processor to execute code instructions, for example, by selecting the treatment plan and/or instructions to operate the skin treatment applicator according to the calculated location, analysis of sensor outputs, and/or analysis of records.

The systems and/or methods described herein improve performance of a computing unit operating the skin treatment applicator, by improving the selection of operation instructions to apply a facial treatment which is customized to the patients.

Accordingly, the systems and/or methods described herein are necessarily rooted in computer technology to overcome an actual technical problem arising in dynamic adaptation of instructions to operate a skin treatment applicator.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Figure 2:
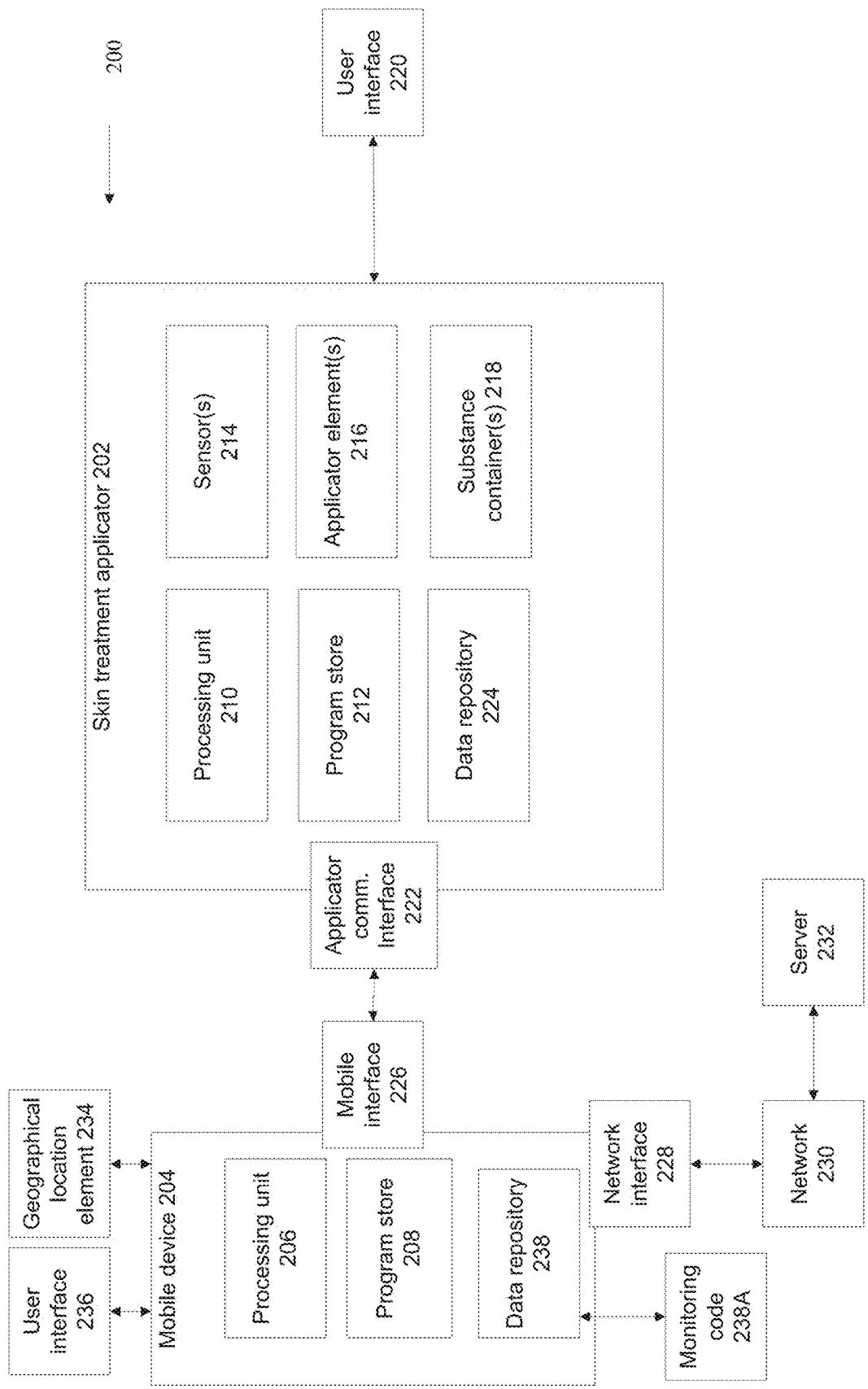
FIG. 2 is a diagram of components of a system that dynamically adapts instructions provided to a skin treatment applicator, in accordance with some embodiments of the present invention.

Reference is now made to FIG. 1, which is a method for dynamically adapting instructions provided to a skin treatment applicator providing a facial treatment to a face of a patient, in accordance with some embodiments of the present invention. The facial treatment may be dynamically adapted based on a location of the skin treatment applicator in front of a facial skin segment of the face of the patient, based on a current facial skin profile of the patient, and/or based on estimated exposure to skin damage factors and/or based on treatments provided to other patients possibly with their results. Reference is also made to FIG. 2, which is a diagram of components of a system 200 that dynamically adapt instructions provided to a skin treatment applicator 202, in accordance with some embodiments of the present invention. The acts of the method of FIG. 1 may be implemented by components of system 200. For example, the instructions may be determined by a mobile device 204 in communication with skin treatment applicator 202, by processing unit 206 of mobile device 204 executing code stored in program store 208, and/or by processing unit 210 of skin treatment applicator 202 executing code stored in program store 212. The code may comprise a mobile application executed by mobile device 204. The application may be a client-server application. Optionally, the treatment is determined remotely, for example, by server 232, and transmitted over network 230 to mobile device 204 and/or skin treatment applicator 202. Server 232 may collect and/or aggregate data from multiple patients using different skin treatment applicators and/or mobile devices, and use the aggregated data to centrally determine the treatment for each patient, for example, by applying a classifier to values determined for each patient, as described herein.

Skin treatment applicator 202 may be hand-held (e.g., by a grip element) and moved along the face and/or a table-top unit (which remains fixed relative to the supporting location, such as a counter or table) in which the user brings their face towards skin treatment applicator 202. Skin treatment applicator 202 may be relatively small, for example the size of 1 US cent coin to the size of a 25 US cent coin. Skin treatment applicator 202 may be designed for home use by the users.

Skin treatment applicator 202 may include one or more sensors 214 (which may be different or similar), which may be fixed and/or removable modular units (e.g., replaceable with other sensors). Sensor(s) 214 may be designed to contact the face of the patient, and/or be positioned in proximity to the face without contacting the face. Sensor(s) 214 may be an imaging sensor that captures still images and/or videos (e.g., at visible light wavelength, at infrared wavelength, and/or other non-visible wavelengths) of the facial segment (and/or face). Sensor(s) 214 may sense (perform direct measurements of, or generate data which is analyzed to obtain) visual skin properties (e.g., color, shade, pigmentation, wrinkles, moles or others), physical skin properties (e.g., elasticity, thickness, topography, oiliness or others), and/or chemical skin properties (e.g., moisture content). Other exemplary sensor(s) 214 may include: skin moisture sensor that estimates the moisture content of the skin segment, and skin elasticity detector that estimates the skin elasticity of the skin segment. Sensor(s) 214 may include a sensing surface that senses the skin by contact with the skin, and/or a sensing element that performs sensing without contact of the skin.

Skin treatment applicator 202 may include one or more applicator elements 216 (which may be similar or different) that apply one or more substances stored within one or more substance container(s) 218 (which may be stored within skin treatment applicator 202, for example, within capsules and/or within small containers, which may be disposable and/or removable for cleaning and refill) to the facial segment according to the determined instructions, for example, apply a cream, a lotion, a serum, hydrating lotion, nutrients, oil, gel, cleaning lotion, water, or other substance or medicament to the facial segment, for example, using a brush, a spray, a dropper, a massager, or the like.

The capsules stored within cosmetic substance container 218 may include a tag indicating the product stored in the capsule, for example, barcode or radiofrequency identification (RFID) which may be read by a tag reader coupled to skin treatment applicator 202. The capsule may also be identified by an electronic element, such as 2 wire memory.

In some embodiments, the capsule may be identified as a new or continued capsule (i.e., a capsule that has been placed, installed or put within the device, removed and later placed again) which contains cosmetic substance therein. The device may be operative in measuring the material remaining in the capsule. The system may report the amount of substance within the capsule, how many treatments or the duration of time for which the substance within the capsule may suffice for. The capsule parameters, such as its type, expiration date or others may be indicated in the database and may be accessible by the user, the device, the capsule provider, the advisory board, or other entities.

Applicator element 216 may deliver energy to the facial segment according to the determined instructions, for example, light, laser, radiofrequency (RF), ultrasound, or others. Applicator elements 216 may be designed to peel the skin, for example, by a rotating member or a fine surface that removes dead skin and/or promotes blood circulation. Applicator element(s) 216 may be modular (e.g., removable and replaceable with other applicator elements) and/or permanent and/or refillable. Applicator 202 may be designed to allow multiple simultaneous applicator elements 216 (activated simultaneously or one at a time according to the instructions), or designed to accommodate one element 216 at a time (allowing removal and replacement with different elements 216, for example, according to the determined instructions). Applicator elements 216 may be permanent or detachable.

In some exemplary embodiments, one or more of the following exemplary setting may be used:
  Laser therapy may be applied using any one or more wavelengths, such as a combination of 852 nanometer and 658 nanometer, for example at 20-100 MilliWatt.
  RF therapy can be applied at intensity of 5-30 Watt and frequency of 0.5-5 MegaHertz (MHz), and electrophoresis can be applied at frequency of 30-200 KiloHertz (KHZ) and intensity of 30-200 volt.

One or more of the exemplary therapies or others may be applied for time periods such as between a few seconds and a few minutes, for example up to about 10 minutes for each treatment type, or up to about 10 minutes altogether.

Applicator elements 216 may be designed, for example, to clean the skin, deliver nutrition to the skin, regenerate the skin, build protein chains, strengthen existing protein chains, reduce melanocytes, reduce free oxidants or other toxins, reduce redness, or the like. Applicator element 216 may be designed to apply one or more treatments, such as: cleaning, pore widening, mechanical or chemical peeling, heating, cooling, massaging, skin stretching, patting, electroporation, or the like.

Applicator elements 216 may include control units (e.g., circuitry) and/or motors (e.g., electric motors) to apply the treatment according to instructions. Alternatively or additionally, the control units and/or motors are located within skin treatment applicator 202, engaging inserted applicator elements 216.

Applicator element(s) and sensor(s) may be independent elements, possibly located at different positions on skin treatment applicator 202 (e.g., independently removable and replaceable), and/or integrated (e.g., removable and/or replaceable together) such as a sensor located within an applicator element.

Skin treatment applicator 202 may include or be in communication with a user interface 220 that allows the patient (or another user) to enter data and/or provides the patient (or other user) with outputted data. For example the user interface may provide and/or receive data using one or more of: a touch-surface such as: a keyboard, a touch-pad, a touch-screen, button(s), dial(s), and/or a microphone (with optional voice recognition software), and/or speaker.

Skin treatment applicator 202 may be powered by batteries (optionally rechargeable), a wall outlet (via a cable and plug), or other methods.

Skin treatment applicator 202 may include an applicator communication interface 222 for communication with mobile device 204, for example, a short range wireless interface, a network interface, a cellular interface, a cable interface, and/or a virtual interface.

Skin treatment applicator 202 may include or be in communication with a data repository 224, which may store, for example, data outputted by sensor(s) 214 for transmission to mobile device 204, to server 232, and/or for processing locally by skin treatment applicator 202 (e.g., acting as a buffer). It is noted that data repository 224 and program store 212 may be separate storage units, and/or integrated within the same storage unit.

Mobile device 204 may include a mobile device interface 226 for communicating with applicator communication interface 222 of skin treatment applicator 202, for example, a wireless communication interface (e.g., Wi-Fi) and/or a cable link. Mobile device interface 226 at least corresponds to interface 222 to allow data transfer between mobile device 204 and skin treatment applicator 202, for example, a short range wireless interface.

Mobile device 204 may include or be in communication with a network interface 228 that connects mobile device 204 to a network 230, for example, a cellular network, the internet, and/or a local area network. Mobile device 204 may communicate with one or more remote servers 232 over network 230, for example, to obtain weather forecasts and/or other data as described herein.

Mobile device 204 may include or be in communication with a geographical location element 234 that outputs data indicative of the physical and/or geographical location of the mobile device, for example, a global positioning system (GPS), or based on electronic signals transmitted over a wireless network indicative of the location of the user.

Mobile device 204 includes or is in communication with a user interface 236 that allows the patient (or another user) to enter data and/or provides the patient (or other user) with outputted data, for example one or more of: a touch-surface such as: a keyboard, a touch-pad, a touch-screen, button(s), dial(s), and/or a microphone (with optional voice recognition software), and/or speaker.

Mobile device 204 may include or be in communication with a data repository 238, which may store, for example, monitoring code 238A as described herein, past treatments and their results, or the like.

Mobile device 204 may be implemented, for example, as a Smartphone, a Tablet computer, a laptop, a wearable device (e.g., computing glasses, watch computer). It is noted that the mobile implementation of mobile device 204 is exemplary and not necessarily limiting. For example, the functions of mobile device 204 may be implemented by a remote server, a desktop computer, a dedicated device, a web server, or other computing units (e.g., over a suitable communication connection between skin treatment applicator 202 via interface 222 or another interface).

Processing unit 206 of mobile device 204 and/or processing unit 210 of skin treatment applicator 202 may be implemented as, for example, a central processing unit (CPU), a graphics processing unit (GPU), field programmable gate arrays (FPGA), digital signal processor (DSP), application specific integrated circuits (ASIC), or others. Processing unit 206 and/or 210 may include one or more processors (homogenous or heterogeneous), which may be arranged for parallel processing, as clusters and/or as one or more multi core processing units. It will be appreciated that some or all processing may be performed by one or more processors associated with server 232. In some embodiments, processing may be divided between processing unit 206 of mobile device 204 and/or processing unit 210 of skin treatment applicator 202 and/or a processor associated with server 232.

Program store 212 of skin treatment applicator 202 and/or program store 208 of mobile device 204 and/or program store associated with server 232 may store code implementable by respective processing units 210 or 206, for example, a random access memory (RAM), read-only memory (ROM), and/or a storage device, for example, non-volatile memory, magnetic media, semiconductor memory devices, hard drive, removable storage, and optical media (e.g., DVD, CD-ROM).

Data repository 224 of skin treatment applicator 202 and/or data repository 238 of mobile device 204 and/or data repository associated with server 232 may be implemented, for example, as a hard drive, removable storage, built-in storage, a remote server, and/or other storage devices.

The dynamic adaptation of the instructions to operating skin treatment applicator 202 may reduce damaging effects of the skin, for example, skin defects due to aging, skin laxity, skin flaccidity, physiology aging, gravitation, elastosis, nasolabial folds, wrinkles, mimic wrinkles, photo aging (i.e., skin defects caused by the sun or other environmental factors), oxidation, wrinkles, rhythids, hyper keratosis, pigmentation, dehydration, and clinical pathology, for example, dermatitis, scars, and acne.

The acts of the method described with reference to FIG. 1 (and/or FIGS. 3, 4, 5) may be entirely performed by skin treatment applicator 202 (i.e., by processing unit 210 executing code stored in program store 212), entirely (or mostly) performed by mobile device 204 (i.e., by processing unit 206 executing code stored in program store 208) based on data outputted from sensors 214 and/or received from skin treatment applicator 202 and transmission of determined instructions for execution by skin treatment applicator 202, and/or shared between skin treatment applicator 202 and mobile device 204, e.g., skin treatment applicator 202 may collect output from sensors 214, and perform initial processing and/or analysis of the data. Mobile device 204 may determine the instructions for execution by skin treatment applicator 202. In some embodiments, a processing unit associated with server 232 may also perform some or all of the computations.

At 102, face related data associated with the patient is received. The data may be associated with a facial segment and/or with the entire face of the patient, with demographic data of the patient such as age or gender, geographic data such as wherein the patient lives, works or vacations, with behavioral data of the patient, or the like. The face related data may be directly associated with the face of the patient, based on measurements performed on the face of the patient, for example acquired images using an image sensor, or estimated moisture content of the skin measured using a moisture sensor. The face related data may be indirectly associated with the face of the patient based on data associated with external parameters that affect the face, which may be obtained and/or measured without the face of the patient, for example, sun ultraviolet (UV) index values, weather, environmental conditions, and the geographical location of the user.

The direct face related data may be provided by sensor(s) 214 of skin treatment applicator 202. The indirect face related data may be collected (e.g., by mobile device 204) from server(s) 232 and/or geographical location element 234 (e.g., by monitoring code 238A) as described herein, for example, environmental data, and location data indicative of location of the user.

Other data such as historic face data, demographic, geographic or behavioral data may be provided by a user, retrieved from a storage device, or the like.

Optionally, the collected data is transmitted to a central repository (e.g., associated with server 232) which stores data collected and/or aggregated from multiple users. The central repository may store the data from each user, optionally along with the determined treatment plan (e.g., as described herein) and/or treatment results (which may be manually entered by the user and/or automatically derived by analyzing data collected in the next iterative cycle and compared to previously collected data). The collected data may be used to train statistical classifiers (e.g., as described herein), to determine treatment plans for patients based on treatment plans that were successful in other users that may have characteristics similar to the present user (e.g., according to a correlation requirement), or additional usages.

At 104, the face related data is analyzed. The data may be analyzed locally by skin treatment applicator 202 and/or by mobile device 204 and/or at a remote location (e.g., server 232). The analysis may be performed based on the outputted sensor data, to identify one or more values of parameters, for example, measuring a current value of a variable skin characteristic of the facial skin of the patient, as described herein.

The data may be analyzed remotely, by a remote server (e.g., server 232), transmitted to the remote location directly to skin treatment applicator 202 (e.g., over a network connection and/or cellular channel) and/or via mobile device 204. The data may be automatically analyzed by the remote server, and/or manually analyzed, for example, by a user (e.g., professional data analyzer, cosmetician, dermatologist).

Data analysis may comprise determining a treatment based on a trend of results following previous treatments provided to the user.

In some embodiments, the treatment may depend on the specific location on the user's face that is being treated. The estimation of the location of the facial skin segment may be performed in response to instructions provided to the user (e.g., visually presented on a display and/or verbally provided using a microphone) to position skin treatment applicator 202 in front of a certain facial skin segment, to verify that the user actually positioned skin treatment applicator 202 at the correct location. The estimation of the location may be performed in response to the user positioning skin treatment applicator 202 without necessarily being instructed.

The estimation of the location may be performed in response to the user pressing a button (e.g., using a GUI presented on a display and/or other buttons or verbal instructions recorded by a microphone) indicating that the user wants to treat the current location and/or that the user reached the instructed location. Alternatively or additionally, the estimation of the location may be performed continuously or periodically to estimate the current location and/or detect changes in location.

Figure 5:
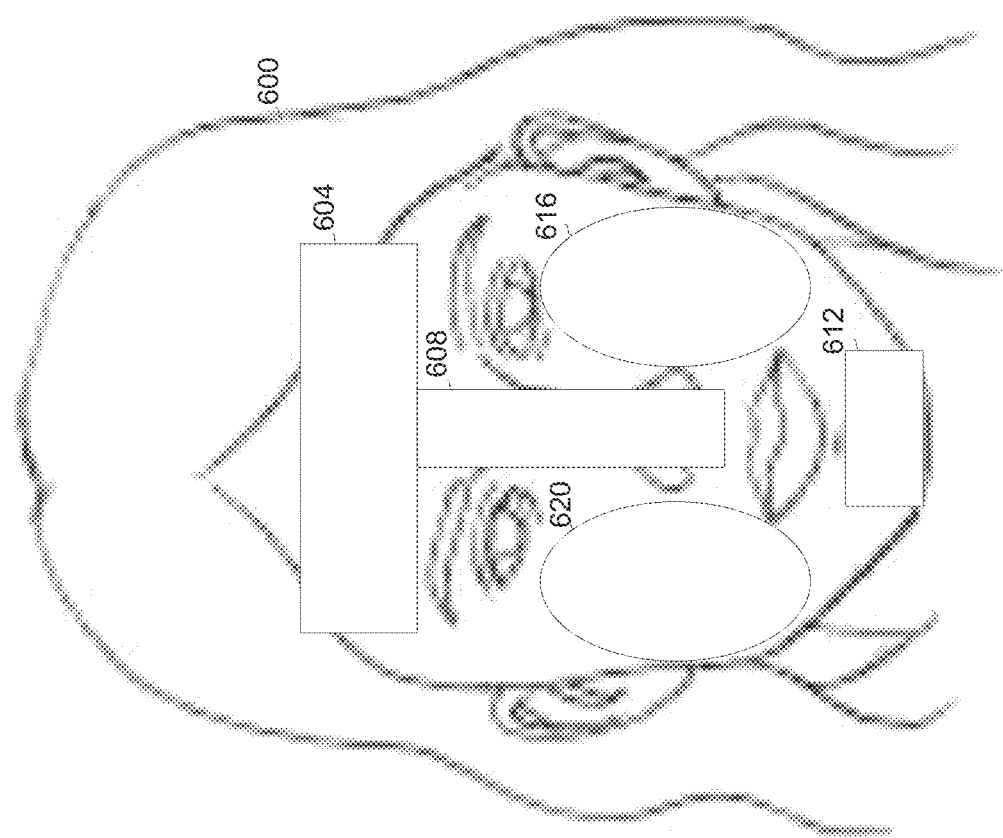
FIG. 5 is a schematic depicting exemplary facial segments, in accordance with some embodiments of the present invention.

Reference is now made to FIG. 5, which is a schematic illustration depicting exemplary facial segments, in accordance with some embodiments of the present invention. A face 600 to be treated is presented. Face 600 may be presented on a display (e.g., user interface 220 and/or 236). The facial segments may be marked (e.g., highlighted or shaded or colored) to indicate to the user where to position skin treatment applicator 202, and/or showing the current location of skin treatment applicator 202. The user may use face display 600 to manually enter the current location of (or where the user intends to position) skin treatment applicator 202, for example, by touching the facial segment on a touch screen and/or clicking the facial segment presented on the display. Exemplary facial segments include forehead 604, nose 608, chin 612, left cheek 616, and right cheek 620.

Alternatively, the current location may be estimated automatically by comparing current measurements to measurements taken in previous occasions in which the user placed the applicator in a location as required. The measurements may include chemical or biological measurements, as well as measurements related to the face structure, such as estimating the shape or the contour of the face area. Thus, the current location may be determined based on the comparison, after which the treatment appropriate for the face part may be applied.

Referring now back to blocks 102-104 of FIG. 1, alternatively or additionally, the instructions to dynamically adapt the facial treatment application by skin treatment applicator 202 may be determined according to a current skin profile of the patient.

Figure 3:
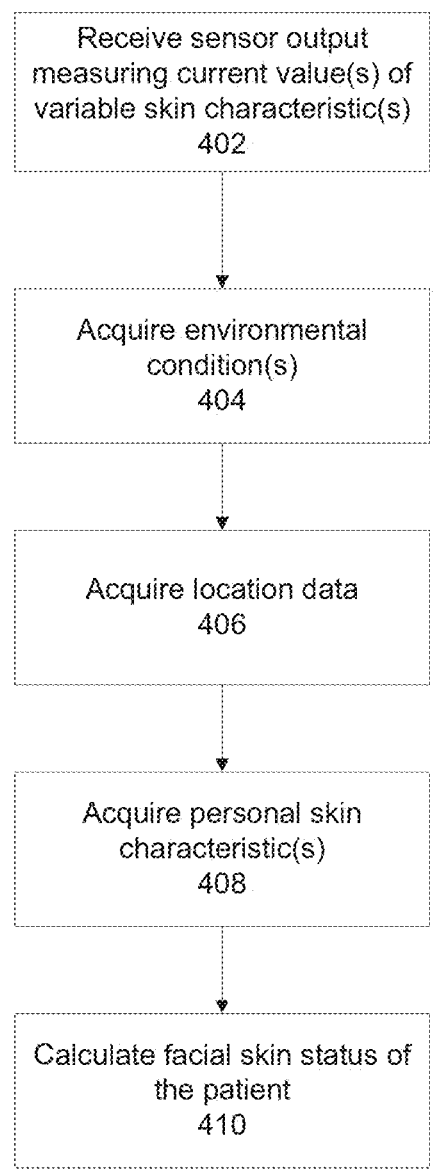
FIG. 3 is a flowchart of a method of determining a current facial skin profile of the patient, in accordance with some embodiments of the present invention.

Reference is now made to FIG. 3, which is a flowchart of a method of determining a current facial skin profile of the patient, in accordance with some embodiments of the present invention. The current facial skin profile may be a collection of one or more absolute and/or relative values representing the current state of the skin of the patient. Treatment may be selected and/or adapted according to the current facial skin profile, and/or according to changes between the current facial skin state and the previous facial skin state. For example, when the current facial skin state represents a worsening in one or more characteristics relative to the earlier facial skin state, the treatment selected may be adjusted to try and improve the facial skin state of the user.

At 402, data outputted from sensor(s) 214 measuring current value(s) of variable skin characteristic(s) of facial skin of a patient is received by skin treatment applicator 202. Variable skin characteristics represent characteristics of the skin of the patient that may vary over time for the same patient, for example, skin moisture content, elasticity, color and/or pigmentation (e.g., due to tanning), or others.

Exemplary sensors 214 measure the variable skin characteristics include imaging sensors (e.g., sensing color and/or pigmentation), skin moisture detector (e.g., sensing skin moisture), and a skin elasticity detector (e.g., sensing elasticity).

Optionally, at 404, one or more environmental condition characteristics are acquired. The environmental condition characteristics represent characteristics that affect the variable skin characteristics of the facial skin of the patient. Exemplary environment condition characteristics include: humidity forecast, temperature forecast, overcast forecast, and ultraviolet index forecast. For example, cold and/or dry weather conditions reduce the skin moisture content and/or reduce skin elasticity. For example, a high ultraviolet index combined with a sunny day may affect the skin color, pigmentation, moisture content, and/or elasticity, for example, by burning the skin.

The environmental condition characteristics may be acquired, for example, by mobile device 204 accessing server 232 over network 230. Sever 232 may be a publicly available platform storing or retrieving the environmental condition characteristics, for example, obtained from meteorological data. The environmental condition characteristics may be measured by applicator 202 or mobile device 204, for example, using built-in or module elements, such as a thermometer, and/or a humidity sensor.

Alternatively or additionally, at 406, location data indicative of a current location of the patient is acquired. The location data may be acquired, for example, from geographical location element 234 (e.g., GPS system), by asking the user to manually enter the location (e.g., presented on a display in communication with mobile device 204), by querying the cellular network to identify the base station mobile device 204 is using for access, by retrieving data and/or from a social network site of the user.

The current location may be analyzed to detect whether the user is located indoors (e.g., within a mall, office, or subway) or outdoors.

The current location may be used to acquire the environmental condition characteristic, for example, the current weather, humidity, pollution level, radiation level, electronic radiation level, and/or UV index measured at the current location of the patient.

Optionally, an analysis of historical records indicative of locations of the patient in a predefined period which precedes the calculating of the current facial skin status is performed. For example, to detect when the patient spent 2 weeks in the sun while travelling in Florida during a vacation, but is now back in the cloudy and cold New York winter. The predefined period may be determined, for example, based on the intervals between facial skin treatments. In this manner, each current treatment may be based on the location of the patient after the previous treatment.

Optionally, an analysis of scheduling records indicative of future locations of the patient in a predefined period which proceeds the calculating of the current facial skin status is performed. For example, when the patient is currently being treated in accordance with a cloudy and cold New York winter, but is expected to go on a 2 week vacation in a warm and sunny climate, the facial treatment may be adapted accordingly, for example, to protect against sun damage.

Optionally, an analysis of the daily, weekly, monthly, and/or yearly routine of the patient in a predefined period which proceeds the calculating of the current facial skin status is performed. For example, when the patient is treated on a summer weekend day, the treatment may take into account longer stay in the sun than in other months or days, and the provided treatment may change accordingly. Similarly, the treatment may change upon the time of the day.

The historical records, the scheduling records, and/or data to determine the historical records and/or the scheduling records (e.g., location data) may be gathered using monitoring code 238A stored in data repository 238 of mobile device 204. The monitoring code 238A may access geographical location element 234, server(s) 232, data stored in data repository 238, and/or other data storage locations.

Alternatively or additionally, at 408, one or more personal skin characteristics of the facial skin of the patient are acquired. The personal skin characteristic may be acquired, for example, by accessing a database of data of the patient stored on a storage device (e.g., on server 232, in data repository 238, on data repository 223) for example medical records, manually entered by the user (e.g., using user interface 236), based on an analysis of data outputted by sensor(s) 214 (e.g., analysis of the image of the face of the patient to determine skin color), and/or based on an analysis of publicly available data of the patient (e.g., accessed from a social network site of the patient). The personal skin characteristics may be acquired based on an analysis of manually entered user data and/or acquired data, for example, based on answers the user provides to predefined questions (e.g., using a graphical user interface presented on a display), for example, do you have lots of freckles? Does your skin dry easily? Do you sunburn easily? Did you sunburn a lot as a child?

Exemplary personal skin characteristics include: skin color, skin shade, genetic information, skin thickness, and skin type.

At 410, a current facial skin status of the patient is calculated according to one or more input parameters: the personal skin characteristic(s), the current value(s) of the variable skin characteristic, the environmental condition characteristic, the location of the user, and the outcome of the analysis of the historical records and/or scheduling records.

The current facial skin status may be calculated and/or represented, for example, as one or more absolute numbers using one or more functions (e.g., weighted function) that receive one or more input parameters, as a relative number calculated based on changes in the one or more input parameters, as a normalized value (e.g., on a scale of 0-1, or 0-100), as a set of values, as a record, as an array, as text parameters, or other representations.

The current facial skin status may be stored (e.g., in data repository 238 and/or 224), for use in determining the instructions to operate skin treatment applicator 202. The current skin status may be stored in a set of current facial skin status values for the patient recorded at different periods over time.

Referring now back to blocks 102-104 of FIG. 1, alternatively or additionally, the instructions to dynamically adapt the facial treatment application by skin treatment applicator 202 are determined based on an estimated exposure to skin damage factors.

Figure 4:
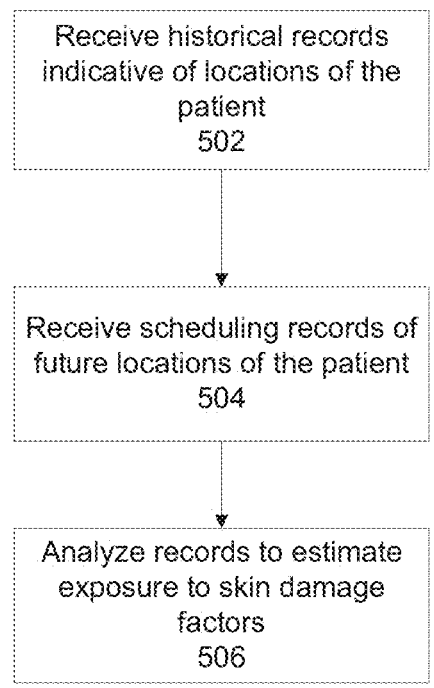
FIG. 4 is a flowchart of a method to estimate exposure to skin damage factors, in accordance with some embodiments of the present invention.

Reference is now made to FIG. 4, which is a flowchart of a method of estimating exposure to skin damage factors, in accordance with some embodiments of the present invention.

At 502, historical records indicative of locations of the patient in a predefined historical period are accessed, for example, as described with reference to block 406 of FIG. 3.

The historical records may be indicative of daily/weekly/monthly/yearly routine of the patient. Additionally, specific routine data may be provided.

At 504, scheduling records indicative of future locations of the patient in a predefined future period are accessed, for example, as described with reference to block 406 of FIG. 3.

The historical records and/or the scheduling records may be gathered using monitoring code 238A (which may be stored in data repository 238 of mobile device 204), for example, as described herein with reference to block 406 of FIG. 3.

At 506, historical records and/or scheduling records are analyzed to estimate the exposure of the patient to skin damage factors. For example, patients that normally live in cooler and/or cloudier climates that take frequent vacations to sunny destinations may be identified as being at high risk to skin damage factors resulting from sun exposure. In another example, patients that live in a region with a very cold climate may be identified as being at high risk for skin damage due to exposure to extreme cold.

A value or metric indicative of cumulative exposure to skin damage factors may be calculated and/or estimated, for example, as a weighted function based on known and/or estimated skin damage factors of the locations of the patient. For example, a patient that lived for many years close to the equator but now lives in a cold and cloudy country may have accumulated significant sun damage.

Referring now back to block 104 of FIG. 1, additional external data may be collected and correlated with the patient related data. The additional external data may be used to train a statistical classifier to determine the treatment plan, as described herein. The additional external data may be collected, for example, from external servers (e.g., storing publicly available data, such as measured radiation levels, and weather data) and/or external sensors accessible to mobile device 204 (e.g., in the home and/or office of the user measuring home or office pollution levels when the user is present).

The user may be prompted to enter additional data manually, for example using a GUI presented on a display (e.g., 220 and/or 236) and/or using a webpage hosted by a website, for example, physical activity performed by the user, fitness activity (e.g., gym attendance), food consumption, alcohol consumption, smoking details (e.g., how many cigarettes a day), sleeping details (e.g., how many hours of sleep a night), age, height, weight, manually entered skin condition (e.g., selected from a list of skin conditions), the patient's perception of their current skin condition (e.g., happy, not happy), lab collected data (e.g., bacteriology analysis), physical measurements (e.g., blood pressure, pulse, blood sugar level), allergies, other medical conditions, and previously tried treatments (e.g., the effectiveness of each treatment, positive or negative). The additional manually entered data may be used to train the statistical classifier for selecting the treatment plan, for example, by identifying other users that are similar (e.g., according to a correlation metric) to the current user, and/or based on other correlations between the manually entered data and the treatment plan (e.g., users eating fatty foods may be more prone to oiler skin, which may help to determine the treatment plan accordingly).

Optionally, the user is prompted (e.g., using the GUI presented on the display, e.g., 220 and/or 236) to enter subjective feedback about the effectiveness of the treatment. For example, responding yes/no (or using a satisfaction scale) to the following questions: Do you feel an improvement in your skin after using the treatment? Are you satisfied with the current state of treatment? Do want to further improve treatment? Do you feel the treatment made your skin worse than without the treatment? The subjective entered data may be used to train the classifier to determine effective treatments. The subjective data may be compared to objective data (e.g., obtained by measurements of the skin using sensors 214) to determine whether the user's perception is based on actual skin changes or not, for example, to identify whether the treatment is actually effective or a result of the placebo effect.

At 106, a treatment plan for the patient is calculated. The treatment plan is calculated according to the location of skin treatment applicator in front of the facial skin segment of the patient, the current facial skin profile as described with reference to FIG. 3, the analysis of the historical records and/or scheduling records (e.g., indicative of estimated exposure to skin damage factors) as described with reference to FIG. 4, and/or other data as described herein (e.g., weight of the patient, blood pressure, alcohol consumption, and exercise).

The treatment plan may include one or more stages. The stages may be selected together, or each stage may be selected based on additional data gathered prior to the application of the stage, and/or the stages may be adapted based on additional gathered data. An exemplary treatment plan may include a preparation stage (e.g., cleaning, port widening) and a treatment stage (e.g., delivery of energy or substance to achieve a treatment effect).

The preparation stage may include instructions to cause a peeling effect to the skin (e.g., using mechanical effects such as a brush, chemical effects by application of a lotion, massage by a massaging element, and/or heating by application of energy from an energy element). Peeling may be applied for example, for 1-20 seconds, or other time periods, optionally per facial segment.

The treatment plan may include a post-treatment stage, which may be selected to narrow the pores. The post-treatment stage may include, for example, application of cold (e.g., by a cooling application element), massage (to relax the pores), applying cosmetic substance, or others.

The treatment plan may include multiple stages, which may be defined according to an order, and/or interleaved (e.g., applied simultaneously). Each stage may define application of treatment by one or more treatment elements, according to a treatment profile (e.g., applied force, how long to apply the treatment, what facial segment to apply the treatment to). Different facial segments may have different stages and/or different treatment plans, and/or share common stages and/or the treatment plan. Each patient is provided with a customized treatment plan. The customized plan may be adjusted according to the current patient conditions, such as the current state of the skin of the patient, as described herein.

The treatment plan may be selected per session and/or to be applied in multiple sessions, for example, single event plan, a daily plan (e.g., morning and evening), a weekly plan, and a monthly plan. The treatment plan may be determined in advance for multiple sessions without adjustment of the plan during the sessions. The treatment plan may be determined for multiple sessions and/or be adjusted at time intervals (e.g., adjusted every treatment session or upon user preference).

The treatment plan may include sub-treatment plans according to facial segments. Each facial segment, or a group of facial segments, may be associated with a sub-treatment plan. For example, due to differences in skin characteristics between facial segments, as discussed herein.

The treatment plan may be presented to the user for authorization, for example, presented on a display (e.g., user interface 236 of mobile device 204) optionally within a graphical user interface (GUI) asking the user to approve download of the instructions of the treatment plan to skin treatment applicator 202. The user may be allowed to manually intervene with the treatment plan. The user may use the GUI to adjust parts of the treatment (e.g., stages), reject stages of the treatment plan, and/or add additional stages of the treatment plan. The user may review the collected data on which the treatment plan is selected. The user may authorize the collected data as correct, mark the data as incorrect (and enter correct data), and/or cancel data. Alternatively, the treatment plan may not be manually tampered with by the user.

As used herein, the term classifier (or statistical classifier) broadly means a predictive model and/or classification machine learning model, for example, a statistical classifier, a regression function, a look-up table, decision tree learning, artificial neural networks, big-data analytical methods, Bayesian networks, or others.

Optionally, the treatment plan is to be calculated by a classifier (e.g., stored as code instructions in data repository 224 and/or 238 and/or on an external server executed 232, by the respective processing unit 210 and/or 206 and/or other) based on a machine learning algorithm(s) that use training data from multiple different patients using different treatment plans. The data from the multiple different patients may be aggregated and analyzed, and used to calculate the treatment plan for the current patient based on the experiences of other patients using other treatment plans (e.g., using clustering methods, such as K-means clustering). It may then be determined the characteristics of which cluster best correlate with those of the user, and suggested or used treatment may be based on the specific cluster, whether the treatment relates to the specific technology, used substance, duration, frequency, power, or any other parameter.

The other patients may have one or more characteristics that correlate with the user (e.g., according to a correlation requirement), for example, age, gender, geographic location, skin profile (e.g., as measured by sensor data), and/or genetic profile.

Alternatively or additionally, the treatment plan is calculated by a classifier (the same or a different classifier) based on a machine learning algorithm(s) that uses training data from the same patient (i.e., for which the treatment plan is being calculated) based on previous experience of the same patient. In this manner, the experiences of other patients are learned to adjust the treatment of the current patient, and/or past experiences of the current patent are learned to adjust the treatment, for example, by preventing repeating earlier mistakes in treatment selection, and/or by repeating past treatments that helped.

The classifier may be trained using a training set of one or more of: the facial skin segment(s) of the different patients and/or previously acquired for the current patient, the current facial skin profile of the different patients and/or previously acquired or the current patient, and historical records and/or scheduling records of the different patients and/or for the current patient.

The classifier may be trained based on data (e.g., as described herein) collected over a range of time, for example, a day, a week, a month, and a year. For example, data collected from each patient at multiple periods of time (e.g., at each treatment session) of the range of time.

Data collected over the range of time may be analyzed (e.g., using clustering methods or other machine learning methods) to identify short term and/or long term trends, for example, application of a certain treatment for 2 years resulted in a statistically significant improvement for patients having certain characteristics (e.g., female office workers aged 50-60). The classifier may be trained to recommend treatments according to the identified long term trends.

At 108, instructions are determined to operate skin treatment applicator 202 according to the treatment plan.

The instructions may define which applicator element(s) 216 apply which treatment and for how long, for example, the order of applicator of treatments, simultaneous applicator of treatments, and/or the frequency of treatments (e.g., apply for 1 minute, stop for 5 minutes, and re-apply for 2 minutes. Different applicator elements 216 may be used individually, simultaneously, and/or at different stages o the treatment.

The instructions to operate the treatment applicator may be automatically selected from a dataset mapping between different instructions to operate the skin treatment applicators and one or more of: facial skin segments, current facial skin profile, estimate sun exposure factors (and/or historical records and/or scheduling records), and/or the calculated combined metric or value representing an aggregation of the facial skin segment, current facial skin profile, and/or estimated sun exposure factor. The instructions and/or the mapping dataset may be stored locally in data repository 238 of mobile device 204, on data repository 224 of skin treatment applicator 202, and/or remotely on a server. The instructions may include automatic instructions (e.g. code or other machine readable formats) for execution by processing unit 210 of skin treatment applicator 202. The instructions may include manual instructions presented to the user, for example, presented on the display of mobile device 204 and/or played to the user using a speaker of mobile device 204. The instructions may be stored, for example, as a script, as compiled code, as a set of values corresponding to parameter, and/or in a human readable format.

Optionally, the instructions include presenting to the patient (e.g., displayed on a display of mobile device 204 and/or skin treatment applicator 202) instructions to input or replace one more selected substances (e.g., cream, fluid, lotion) optionally having selected concentration or dosage, or insert one or more capsule containing the selected lotion (s) into cosmetic substance container 218 of skin treatment applicator 202. The presence of the cosmetic substance may be automatically detected by skin treatment applicator 202 (e.g., using the tag or other methods) and/or manually entered by the user (e.g., using a GUI or other button confirming the presence of the cosmetic substance in cosmetic substance container 218).

Optionally, the instructions to operate skin treatment applicator 202 include instructions to control the amount of each substance, the required concentration, type of administration of the substance (e.g., directly to the skin, as a spray, as a cream rubbed into the skin, such as by respective application elements 216), and/or a combination of one or more of the applied substances (e.g., which lotions or other substances to combine, percentage of each substance in the combination, how to combined such as apply a first substance then a second substance or mix the first and the second before application). Skin treatment applicator 202 may include a mixing element to mix the amount of each cosmetic substance according to the instructions, for example, 40% of a first substance and 60% of a second substance.

When the selected cosmetic substance is not currently present within cosmetic substance container 218, the user may be prompted to insert the selected cosmetic substance into cosmetic substance container 218, for example, by a visual message presented on a display and/or audio instructions played by a microphone (e.g. user interface 220 of skin treatment applicator 202 and/or user interface 236 of mobile device 204).

Alternatively or additionally, the instructions to operate the treatment applicator include instructions to adapt an applied light or laser transmission pattern applied by laser and/or light source implementation of applicator element 216. One or more parameters of the applied light or laser transmission pattern are adapted. The parameter(s) include one or more of: frequency, timing, phase, and/or amplitude.

Alternatively or additionally, the instructions include instructions to adapt a radio frequency (RF) transmission pattern applied by an RF source implementation of applicator element 216. One or more parameters of the RF transmission pattern are adapted, including: frequency, timing, phase, and/or amplitude.

Alternatively or additionally, the instructions include instructions to adapt an ultrasonic transmission pattern applied by an ultrasound source implementation of applicator element 216. One or more parameters of the ultrasonic transmission pattern are adapted, including: frequency, timing, phase, amplitude, cleaning intensity, and/or pore widening intensity.

The instructions to operate the treatment application may include instructions to heat the skin, for example, by controlling the application of RF, light, laser, or other energy application. The heating may be selected to increase blood circulation and/or widen pores. The heating may be selected to improve absorbance of selected cosmetic agents applied by the skin treatment applicator.

The instructions may include instructions to apply a local massage to the facial segment by a massaging applicator element(s) 216, for example, a ball, a rolling ball, a revolving member, a brush, a non-smooth surface, or other elements. The massage applicator elements 216 are designed (e.g., direction of motion, surface features) to apply, for example, skin stretching, local pressure, patting, and electroporation. The massage may be selected to promote cell regeneration, for example, by applying the massage before, after, and/or simultaneously with application of cosmetic agents.

At 110, skin treatment applicator 202 is instructed according to the determined instructions. The determined instructions may be transmitted by mobile device 204 to skin treatment applicator 202 over the short range wireless communication channel (e.g., established between mobile interface 226 and applicator communication interface 222). The instructions may be stored in program store 212 and executed by processing unit 210 of skin treatment applicator 202, for example, by activating one or more application elements 216 according to the treatment plan, to apply energy and/or cosmetic substances.

It is noted that when the communication channel between skin treatment applicator 202 and mobile device 204 is not available, the last treatment and/or previously used instructions may be used to apply treatment. When communication is restored, the updated instructions may be downloaded from mobile device 204 and implemented.

Optionally, the instructions include supplemental instructions to present recommendations to the user, which are not implemented by skin treatment applicator 202, for example, to rest, to drink fluids, and to remain in the shade. The supplemental instructions may include recommendations to visit a skin specialist, such as a dermatologist, or cosmetician, for example, when analysis of the data (e.g., block 104) indicates a deterioration over time in view of applied treatments. The collected and/or analyzed data may be transmitted to a remote server for viewing and/or analysis by specialists.

The supplemental instructions may be presented to the user using a GUI presented on a display and/or audio instructions played using a microphone (e.g., user interface 220 and/or 236). The supplemental instructions may be a manual stage within the determined treatment plan, for example, instructing the user to wash the face. The user may use the GUI to indicate when the manual stage is completed. Skin treatment applicator 202 may automatically administer skin treatment before and/or after and/or simultaneously with the manual stage.

At 112, one or more of blocks 102-110 are iterated, to adjust the treatment plan and/or select a new treatment plan. New and/or adjusted instructions are provided to skin treatment applicator 202.

The iteration of blocks 102-110 may be performed, for example, as the user is moving skin treatment applicator 202 across their face to different facial segments (e.g., to deliver different portions of the treatment plan to the different facial segments), per activation of skin treatment applicator 202 to deliver treatment (e.g., once a day, once a week, once a month), and/or at other periods of times and/or according to other events.

The iterations of one or more blocks 102-110 may be considered a loop repeated to monitor the skin condition of the patient, adjust treatment plans, and/or apply treatment plans over time, for example, once a day, once a week, once a month, according to user selection, and/or based on events (e.g., significant changes in skin condition and/or environmental characteristics).

Optionally, some blocks are iterated to monitor the status of the skin of the patient, without necessarily applying treatment. For example, blocks 102-104 are iterated to monitor the current facial status of the patient. The treatment plan may be determined and/or adjusted (e.g., blocks 106-110) according to a requirement, for example, when the current facial status of the patient statistically significantly (e.g., measured by a correlation function) changed relative to one or more previous status measurements.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

It is expected that during the life of a patent maturing from this application many relevant skin treatment applicators, sensors, application elements, and mobile devices will be developed and the scope of the terms skin treatment applicators, sensors, application elements, and mobile devices are intended to include all such new technologies a priori.

As used herein the term "about" refers to ±10%.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A computer implemented method of adapting a facial treatment based on a current facial skin profile, comprising:
    using at least one sensor for measuring at least one current value of at least one variable skin characteristic of facial skin of a patient;
    acquiring at least one personal skin characteristic of facial skin of the patient;
    calculating a current facial skin status of the patient according to the at least one personal skin characteristic and the at least one current value;
    calculating according to the current facial skin status a treatment plan defining how to operate each of a plurality of treatment applicator elements in multiple different stages; and
    operating one or more of the plurality of treatment applicator elements according to the treatment plan such that at least one treatment applicator element from the plurality of treatment applicator elements is operated simultaneously with another one of the plurality of treatment elements that applies a substance in at least one of the multiple different stages;
    wherein the multiple different stages include an RF treatment stage and a laser therapy stage and the plurality of treatment applicator elements comprises an applicator element for the RF treatment stage and an applicator element for the laser therapy stage.

2. The method of claim 1, wherein calculating the current facial skin status of the patient is performed based on code executing a machine learning algorithm trained using a training set storing at least one facial skin characteristic for each of a plurality of different patients.

3. The method of claim 2, wherein the training set stores at least one calculated current facial skin status of each of the plurality of different patients, calculated based on at least one measured current value for at least one variable skin characteristic and at least one personal skin characteristic of each respective patient.

4. The method of claim 1, further comprising acquiring at least one environmental condition characteristic; wherein the current facial skin status of the patient is calculated according to the at least one personal skin characteristic and the at least one current value and the at least one environmental condition characteristic, the at least one environment condition characteristic selected from the group consisting of: humidity forecast, temperature forecast, overcast forecast, pollution level, radiation level, and ultraviolet index forecast.

5. The method of claim 4, further comprising acquiring location data indicative of a current location of the patient and using the current location for acquiring the at least one environmental condition characteristic.

6. The method of claim 1, further comprising performing an analysis of historical records indicative of locations of the patient in a predefined period which precedes the calculating of the current facial skin status; wherein the current facial skin status of the patient is calculated according to the at least one personal skin characteristic and the at least one current value and an outcome of the analysis.

7. The method of claim 1, further comprising performing an analysis of scheduling records indicative of future locations of the patient in a predefined period which proceeds the calculating of the current facial skin status; wherein the current facial skin status of the patient is calculated according to the at least one personal skin characteristic and the at least one current value and an outcome of the analysis.

8. The method of claim 1, wherein the at least one sensor comprises a member of a group consisting of: an image sensor, a skin moisture detector, and a skin elasticity detector.

9. A system for adapting a facial treatment based on a current facial skin profile, comprising:
at least one sensor for measuring at least one current value of at least one skin characteristic of the facial skin of the patient;
a treatment applicator comprising:
a plurality of applicator elements for applying a plurality of different treatments to facial skin of a patient,
a communication unit for receiving data from a database storing data associated with a plurality of patients,
a program store storing code, and
a processor coupled to the communication unit, and to the program store for implementing the stored code, the code comprising:
code instructions for acquiring at least one personal skin characteristic of facial skin of the patient from the at least one current value,
code instructions for calculating a current facial skin status of the patient according to the at least one personal skin characteristic and to the data associated with the plurality of patients,
code instructions for calculating according to the current facial skin status a treatment plan defining how to operate each of a plurality of treatment applicator elements in multiple different stages; and
code instructions for operating one or more of the plurality of treatment applicator elements according to the treatment plan such that at least one treatment applicator element from the plurality of treatment applicator elements is operated simultaneously with another one of the plurality of treatment elements that applies a substance in at least one of the multiple different stages;
wherein the multiple different stages include an RF treatment stage and a laser therapy stage and the plurality of treatment applicator elements comprises an applicator element for the RF treatment stage and an applicator element for the laser therapy stage.

10. The method according to claim 1, wherein operating the one or more determined treatment applicator elements according to the treatment plan include instructions to control at least one of the plurality of treatment applicator elements to change at least one of: amount of the one or more substances, type of the one or more substances, concentration of the one or more substances, and combination of the one or more substances.

11. The method according to claim 1, wherein instructions for operating the one or more determined treatment applicator elements according to the treatment plan include instructions to change the combination of the one or more substances.

12. The method according to claim 1, wherein the method comprises presenting the treatment plan to a user for authorization.

13. The method according to claim 12, wherein the user is allowed to manually intervene with the treatment plan.

14. The method according to claim 12, wherein the instructions are adapted dynamically wherein the treatment plan cannot be manually tampered with by the user.

15. The system according to claim 9, wherein the plurality of treatments further comprises electrophoresis.

16. The system according to claim 9, wherein the instructions to operate the treatment applicator include instructions to adapt at least one parameter selected from the group consisting of: frequency, timing, phase, and amplitude, to adapt:
a radiofrequency (RF) transmission pattern; and
an applied light or laser transmission pattern.

17. The system according to claim 9, wherein the instructions to operate the one or more applicator elements include instructions to control at least one of:
amount, type, concentration, and combination of at least one applied substance.

18. The system according to claim 9, wherein the instructions to operate the one or more applicator elements include instructions to control application of a combination of applied substances.

19. The system according to claim 9, wherein the code comprises instructions to:
calculating a treatment plan, wherein the instructions are determined according to the calculated treatment plan; and
presenting the treatment plan to a user for authorization.

20. The system according to claim 19, wherein the user is allowed to manually intervene with the treatment plan.

21. The system according to claim 19, wherein the instructions are adapted dynamically wherein the treatment plan cannot be manually tampered with by the user.

* * * * *